United States Patent
Kao et al.

(10) Patent No.: US 10,064,768 B2
(45) Date of Patent: Sep. 4, 2018

(54) Y-SHAPED GAUZE POSITIONING ASSEMBLY

(71) Applicant: I-Shou University, Kaohsiung (TW)

(72) Inventors: Yu-Lin Kao, Kaohsiung (TW); Yu-Shiuan Zheng, Kaohsiung (TW); Nien-Hsun Lin, Kaohsiung (TW); Yu-Ting Wu, Kaohsiung (TW); Pei-Rung Liu, Kaohsiung (TW); Pei-Hsing Tseng, Kaohsiung (TW); Yu-Han Huang, Kaohsiung (TW); Han-Chun Liu, Kaohsiung (TW); Yu-Hua Lin, Kaohsiung (TW); Chia-Chan Kao, Kaohsiung (TW)

(73) Assignee: I-SHOU UNIVERSITY, Kaohsiung (TW)

( * ) Notice: Subject to any disclaimer, the term of this patent is extended or adjusted under 35 U.S.C. 154(b) by 0 days.

(21) Appl. No.: 15/430,557

(22) Filed: Feb. 13, 2017

(65) Prior Publication Data

US 2017/0312150 A1 Nov. 2, 2017

(30) Foreign Application Priority Data

Apr. 27, 2016 (TW) .................... 105205963

(51) Int. Cl.
*A61F 15/00* (2006.01)
*A61F 13/00* (2006.01)
*A61M 16/04* (2006.01)

(52) U.S. Cl.
CPC ...... *A61F 15/005* (2013.01); *A61F 13/00029* (2013.01); *A61F 15/001* (2013.01); *A61M 16/047* (2013.01); *A61F 2013/00412* (2013.01); *A61M 16/0497* (2013.01)

(58) Field of Classification Search
CPC .... A61F 13/00; A61F 13/00029; A61F 15/00; A61F 15/001; A61F 15/005; A61F 19/00; A61F 19/001; A61F 19/02; A61F 2013/00412; A61M 16/04; A61M 16/047; A61M 16/0497
USPC ........... 206/363–369; 433/136, 138; D8/137; 15/244.1
See application file for complete search history.

(56) References Cited

U.S. PATENT DOCUMENTS

| 938,421 | A | * | 10/1909 | Hakins | A47L 13/257 15/244.1 |
|---|---|---|---|---|---|
| 1,010,147 | A | * | 11/1911 | Ivory | A61C 19/001 433/138 |
| 5,222,600 | A | * | 6/1993 | Stoddard | A61L 2/26 206/369 |
| D676,732 | S | * | 2/2013 | Lafond | D8/107 |
| 8,979,812 | B2 | | 3/2015 | Loescher | |

(Continued)

FOREIGN PATENT DOCUMENTS

| CN | 203816012 | 9/2014 |
|---|---|---|
| TW | 201021863 | 6/2010 |

*Primary Examiner* — Bryon Gehman
(74) *Attorney, Agent, or Firm* — JCIPRNET

(57) ABSTRACT

A Y-type gauze positioning rod is adapted to be disposed in a Y-type gauze so as to position the Y-type gauze to an affected region. The Y-type gauze positioning rod includes a Y-type flexible body having a holder and two supporting branches. The two supporting branches are connected to the holder and separated from each other. A Y-type gauze positioning assembly is further provided.

6 Claims, 5 Drawing Sheets

(56) References Cited

U.S. PATENT DOCUMENTS 9,387,060 B2 * 7/2016 Talavera-Peraza .......................... A61C 19/001
2009/0320852 A1 12/2009 Cuevas et al.

* cited by examiner

Y-SHAPED GAUZE POSITIONING ASSEMBLY

CROSS REFERENCE TO RELATED APPLICATION

This application claims the priority benefit of Taiwan application serial no. 105205963, filed on Apr. 27, 2016. The entirety of the above-mentioned patent application is hereby incorporated by reference herein and made a part of specification.

BACKGROUND OF THE INVENTION

1. Field of the Invention

The present invention generally relates to a positioning rod and a positioning assembly, in particular, to a Y-type gauze positioning rod and a Y-type gauze positioning assembly.

2. Description of Related Art

Currently, the patient needs to have an artificial tracheostomy tube placed near the intersection of the neck and the clavicle due to dyspnea, or needs to place a blood drainage tube for treatment such as surgery. Y-type gauze is generally used to isolate this kind of living and medical treatment tubes, such as the artificial tracheostomy tube, the blood drainage tube and so on, from the skin so as to absorb secretions and avoid skin friction damage.

In general, the caregiver needs to replace at least one Y-shaped gauze daily. However, the trouble in replacing the Y-shaped gauze is that if the portion where the Y-gauze is to be placed is a curved portion such as a neck, while replacing the Y-type gauze, the caregiver needs to raise the tracheostomy tube by hand or bamboo sticks so that Y-type gauze is able to pass through the space between the tracheostomy tube and the skin of the neck and then be positioned. However, raising or moving the tracheostomy tube may cause the patient uncomfortable easily, more replacing time-consuming and respiratory tract infection.

SUMMARY OF THE INVENTION

The invention is directed to a Y-type gauze positioning rod is capable of placing a Y-type gauze to an affected region easily.

The invention is directed to a Y-type gauze positioning assembly having the Y-type gauze positioning rod.

A Y-type gauze positioning rod adapted to be disposed in a Y-type gauze includes a Y-type flexible body having a holder and two supporting branches wherein the two supporting branches are connected to the holder and separated from each other.

According to an embodiment of the invention, the Y-type gauze comprises a gauze body and a cutting notch, the gauze body is folded to form a multi-layer structure having at least one crease, the cutting notch extends from an edge of the gauze body where the at least one crease exists to a center of the gauze body so as to form two gauze branches, when the Y-type gauze positioning rod is disposed in the multi-layer structure of the Y-type gauze, the two supporting branches of the Y-type gauze positioning rod are located in the two gauze branches of the Y-type gauze, and a part of the holder is exposed from the Y-type gauze.

According to an embodiment of the invention, a concave is located between the two supporting branches separated with each other, a depth of the concave is greater than a length of the cutting notch of the Y-type gauze.

According to an embodiment of the invention, a width of a portion of the concave corresponding to a bottom of the cutting notch ranges between 0.5 centimeter and 1 centimeter.

According to an embodiment of the invention, the two supporting branches forms a V shape or a U shape.

A Y-type gauze positioning assembly includes a Y-type gauze and a Y-type gauze positioning rod disposed in the Y-type gauze. The Y-type gauze positioning rod includes a Y-type flexible body having a holder and two supporting branches wherein the two supporting branches are connected to the holder and separated from each other.

According to an embodiment of the invention, the Y-type gauze comprises a gauze body and a cutting notch, the gauze body is folded to form a multi-layer structure having at least one crease, the cutting notch extends from an edge of the gauze body where the at least one crease exists to a center of the gauze body so as to form two gauze branches, when the Y-type gauze positioning rod is disposed in the multi-layer structure of the Y-type gauze, the two supporting branches of the Y-type gauze positioning rod are located in the two gauze branches of the Y-type gauze, and a part of the holder is exposed from the Y-type gauze.

According to an embodiment of the invention, a concave is located between the two supporting branches separated with each other, a depth of the concave is greater than a length of the cutting notch of the Y-type gauze.

According to an embodiment of the invention, a width of a portion of the concave corresponding to a bottom of the cutting notch ranges between 0.5 centimeter and 1 centimeter.

According to an embodiment of the invention, the Y-type gauze comprises an entrance away from the cutting notch, and the two supporting branches of the Y-type gauze positioning rod is adapted to move into or out of the Y-type gauze from the entrance.

According to an embodiment of the invention, the two supporting branches forms a V shape or a U shape.

According to an embodiment of the invention, the Y-type gauze positioning assembly further includes an outer packaging, wherein the Y-type gauze and the Y-type gauze positioning rod are packaged by the outer packaging and adapted to be sterilized along with the outer packaging.

Based on the above, in the Y-type gauze positioning assembly of the invention, the Y-type gauze positioning rod is disposed in the Y-type gauze as a frame. When user would like to place the Y-type gauze to the affected area, he/she only need to push the Y-type gauze positioning rod disposed in the Y-type gauze so that the Y-type gauze is moved accordingly. The Y-type flexible body of the Y-type gauze positioning rod is able to deform slightly along an outline of the affected area, therefore even a shape of the affected area is a curve, the Y-type gauze still can be moved to the affected area easily by the Y-type gauze positioning rod without raising an artificial tracheostomy tube or a blood drainage tube. In addition, the part of the holder exposed from the Y-type gauze, the user is able to pull out the Y-type gauze positioning rod directly after placing the Y-type gauze to the affected area, so that the Y-type gauze positioning rod can be removed easily. Moreover, the Y-type gauze is able to be packaged and sterilized with the Y-type gauze positioning rod so as to be combined and sold as the Y-type gauze positioning assembly.

In order to make the aforementioned and other features and advantages of the invention comprehensible, several exemplary embodiments accompanied with figures are described in detail below.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
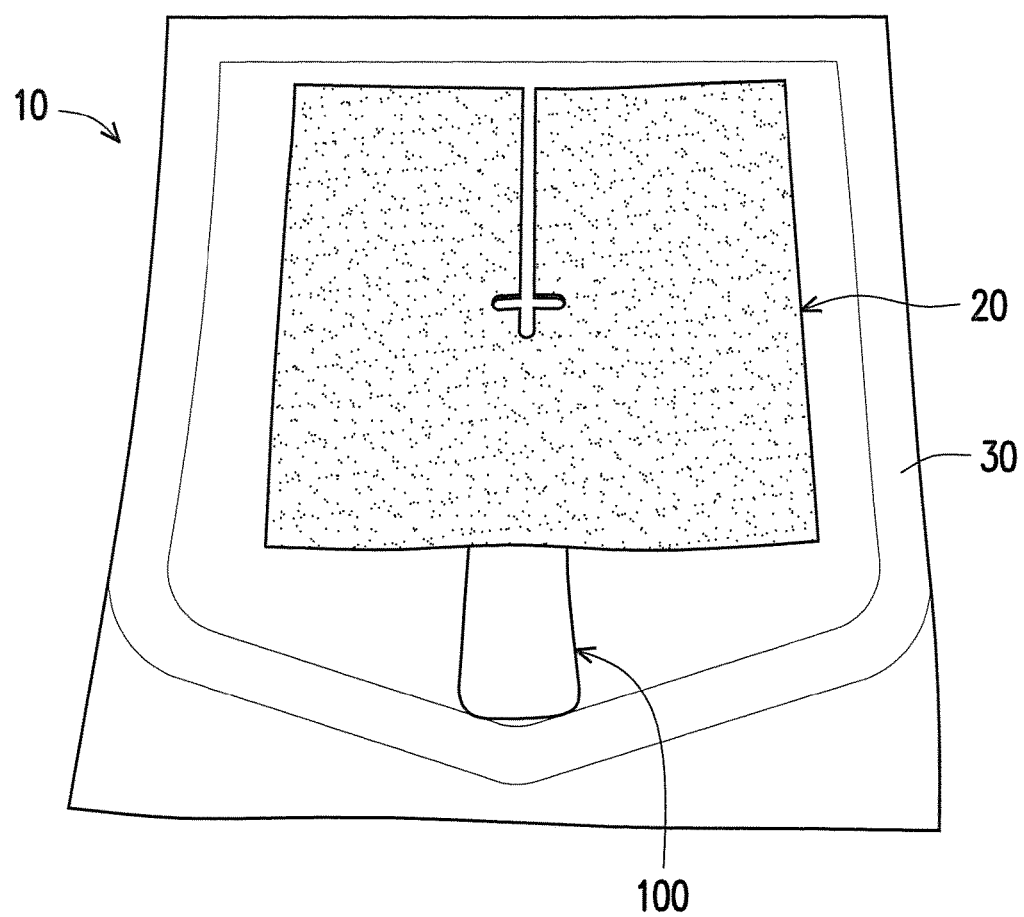
FIG. 1 is a schematic view illustrating a Y-type gauze positioning assembly according to an embodiment of the invention.

Reference will now be made in detail to the present preferred embodiments of the invention, examples of which are illustrated in the accompanying drawings. Wherever possible, the same reference numbers are used in the drawings and the description to refer to the same or like parts.

Generally speaking, when the caregiver places a Y-shaped gauze to a curved portion such as neck and so on, the caregiver needs to raise the tracheostomy tube by hand or bamboo sticks due to space limitation between the tracheostomy tube and the skin of the neck, so that Y-type gauze is able to pass through the space between the tracheostomy tube and the skin of the neck. However, this kind of motion may causes the patient uncomfortable easily and respiratory tract infection. The Y-type gauze positioning assembly 10 and the Y-type gauze positioning rod 100 of the invention are able to assist to place the Y-type gauze 20 to an affected area without moving the tracheostomy tube, the detail would be introduced as below.

FIG. 1 is a schematic view illustrating a Y-type gauze positioning assembly according to an embodiment of the invention. Referring to FIG. 1, the Y-type gauze positioning assembly 10 of the embodiment includes a Y-type gauze 20, a Y-type gauze positioning rod 100 and an outer packaging 30. As shown in FIG. 1, the Y-type gauze 20 and the Y-type gauze positioning rod 100 are both packaged by the outer packaging 30 and can be sterilized with the outer packaging 30. While using, user only needs to open the outer packaging 30, take the Y-type gauze 20 and the Y-type gauze positioning rod 100 out together, and then start to put the Y-type gauze 20 to a specific position by the Y-type gauze positioning rod 100. Certainly, in another embodiment, the Y-type gauze positioning rod 100 and the Y-type gauze 20 also can have their own packages individually and separately, the type of the outer package 30 is not limited thereto.

Figure 2:
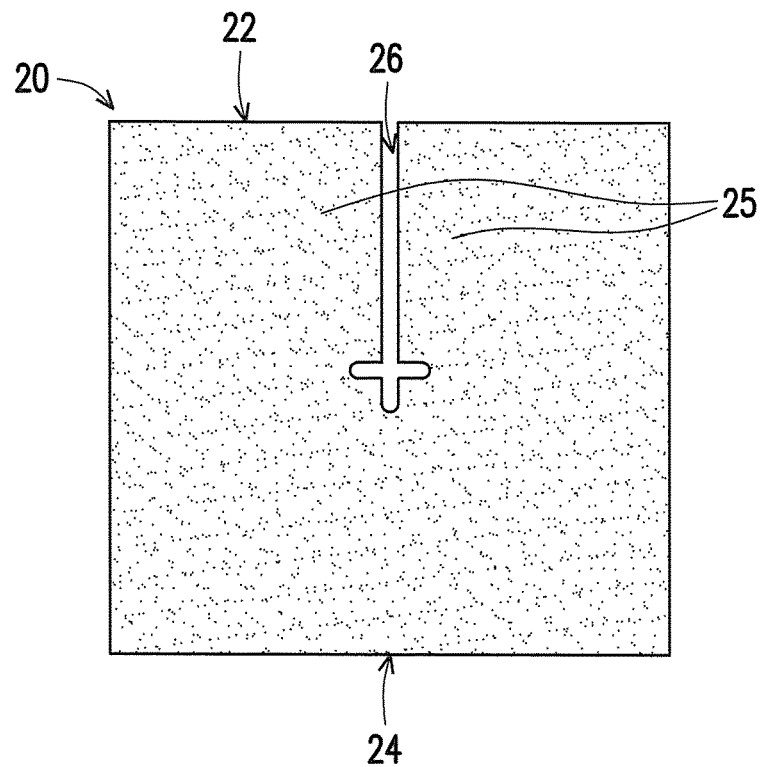
FIG. 2 is a schematic view illustrating a Y-type gauze of the Y-type gauze positioning assembly of FIG. 1.
Figure 4:
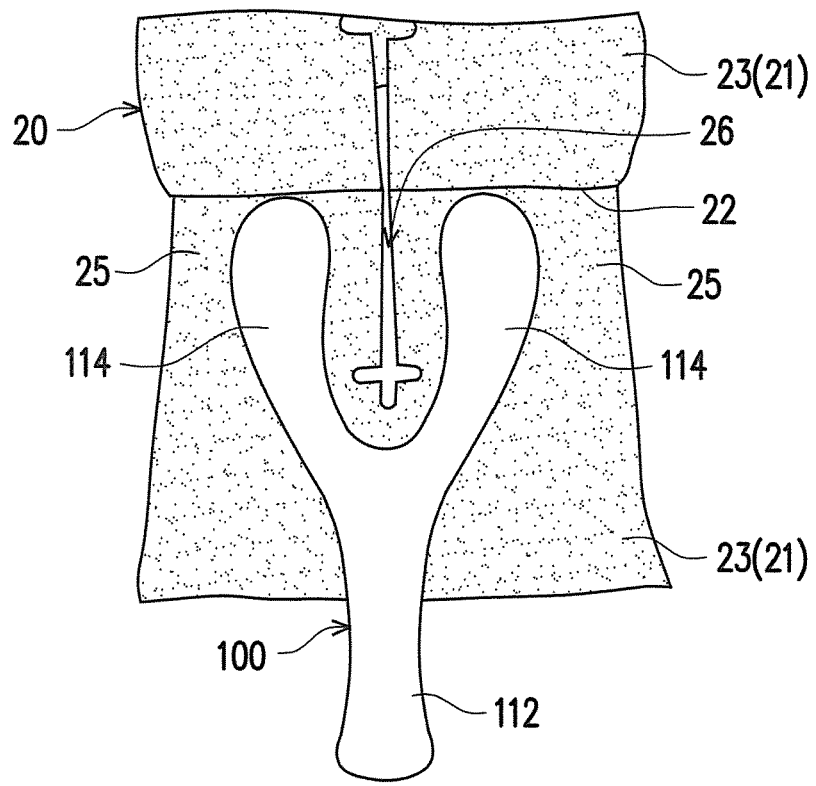
FIGS. 4 and 5 are schematic views illustrating the Y-type gauze and the Y-type gauze positioning rod of the Y-type gauze positioning assembly of FIG. 1.

FIG. 2 is a schematic view illustrating a Y-type gauze of the Y-type gauze positioning assembly of FIG. 1. FIG. 4 is schematic view illustrating the Y-type gauze and the Y-type gauze positioning rod of the Y-type gauze positioning assembly of FIG. 1. Referring to FIGS. 2 and 4 at the same time, in the embodiment, the Y-type gauze 20 includes a gauze body 21 and a cutting notch 26. As shown in FIG. 4, the gauze body 21 is folded to form a multi-layer structure 23 having at least one crease 22. The cutting notch 26 extends from an edge of the gauze body 21 where the at least one crease 22 exists to a center of the gauze body 21 so as to form two gauze branches 25. It is noted that, although FIG. 4 only simply illustrates the gauze body 21 folded as a two-layer structure, in fact, the gauze body 21 can be folded to a multi-layer structure which is more than two layers. As long as the cutting notch 26 is manufactured from an edge of the multi-layer structure 23 where the last crease 22 exists to a center of the multi-layer structure 23, a number of layer of the multi-layer structure 23 is not limited thereto. In addition, the Y-type gauze 20 is able to adopt a product sold in the market, and a shape of the cutting notch 26 is not limited thereto.

Figure 3:
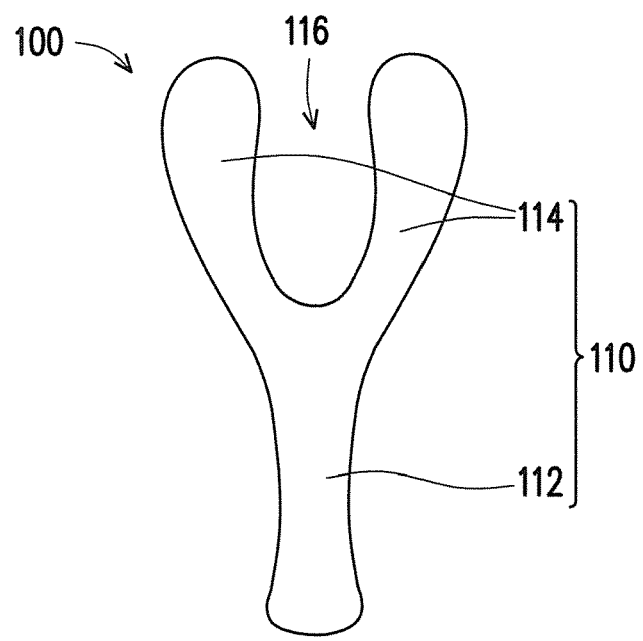
FIG. 3 is a schematic view illustrating a Y-type gauze positioning rod of the Y-type gauze positioning assembly of FIG. 1.

FIG. 3 is a schematic view illustrating a Y-type gauze positioning rod of the Y-type gauze positioning assembly of FIG. 1. Referring FIG. 3, the Y-type gauze positioning rod 100 of the embodiment includes a Y-type flexible body 110. The Y-type flexible body 110 includes a holder 112 and two supporting branches 114. The two supporting branches 114 are connected to the holder 112 and separated with each other.

In the embodiment, material of the Y-type flexible body 110 may be SEPPA material or flexible plastic, silicone or rubber, etc. In other embodiment, material of the Y-type flexible body 110 may be cardboard. Material of the Y-type flexible body 110 should be flexible so as to bend or deform along an outline of the affected area and be capable of providing support.

In addition, in the embodiment, the Y-type flexible body 110 is a flat shape structure so as to lower a whole thickness of the Y-type gauze positioning assembly 10. The thickness of the Y-type flexible body 110 can be preferably less than 1.5 centimeter, and the thickness of the Y-type flexible body 110 can be less than 1 centimeter. Certainly, in another embodiment, the Y-type flexible body 110 also cannot be the flat shape structure. However, because degree of flexibility may be influenced by the thickness of the Y-type flexible body 110, material of the Y-type flexible body 110 need to be softer while the Y-type flexible body 110 is not formed as the flat shape structure so that the Y-type flexible body 110 can be bent along the outline of the affected area. It is noted that, the Y-type flexible body 110 still needs to have a certain degree of supporting property under the premise of flexibility.

Figure 5:
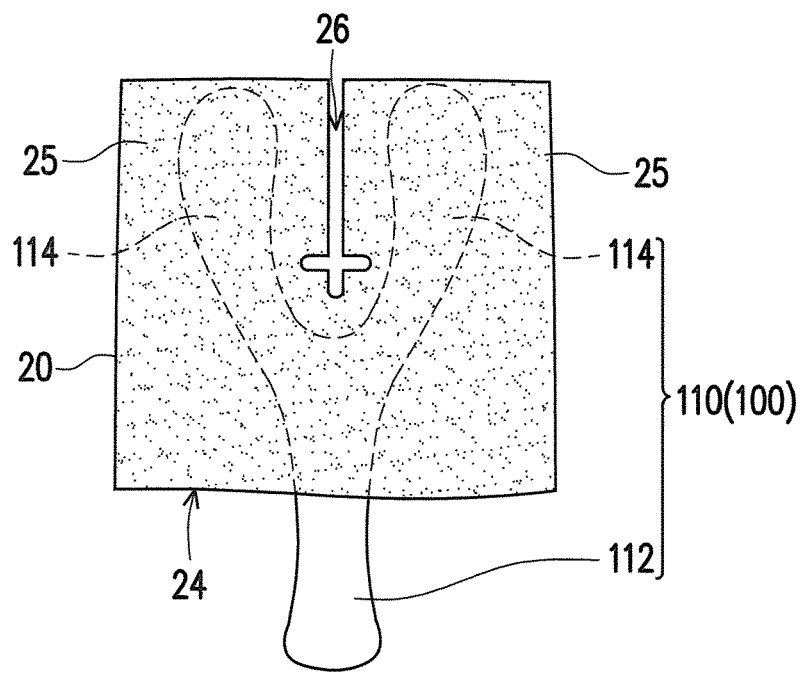

FIGS. 4 and 5 are schematic views illustrating the Y-type gauze and the Y-type gauze positioning rod of the Y-type gauze positioning assembly of FIG. 1. Referring to FIGS. 4 and 5, in the embodiment, the Y-type gauze positioning rod 100 is disposed in the Y-type gauze 20. More specifically, when Y-type gauze positioning rod 100 is disposed in the multi-layer structure 23 of the Y-type gauze 20, the two supporting branches 114 of the Y-type gauze positioning rod 100 are located in the two gauze branches 25 of the Y-type gauze 20, and a part of the holder 112 is exposed from the Y-type gauze 20.

As shown in FIG. 4, a depth of the concave 116 of the Y-type gauze positioning rod 100 is greater than a length of the cutting notch 26 of the Y-type gauze 20 so as to prevent the Y-type gauze positioning rod 100 being exposed from the cutting notch 26. In addition, in the embodiment, a width of a portion of the concave 116 of the Y-type gauze positioning rod 100 corresponding to a bottom of the cutting notch 26 of the Y-type gauze 20 (i.e. a cross portion in the Figure) ranges between 0.5 centimeter and 1 centimeter. Because the width of the portion of the concave 116 of the Y-type gauze positioning rod 100 corresponding to the bottom of the cutting notch 26 of the Y-type gauze 20 is great enough so that the Y-type gauze positioning rod 100 can be widely applied to tubes with different diameters on patients. In other words, basically, during a positioning process of the Y-type gauze positioning assembly 10, all kinds of tubes currently used on patients are able to slide into the concave 116 of the Y-type gauze positioning rod 100. Therefore, the Y-type gauze positioning assembly 10 can be applied to all kinds of tubes currently used on patients.

It is worth to mention that, in the embodiment, the two supporting branches 114 form a U shape, and the concave 116 between the two supporting branches 114 separated with each other also forms a U shape. Distances between the two supporting branches 114 at different cross sections perpendicular to extension direction of the two supporting branches 114 are similar, the two supporting branches 114 substantially extend to a direction away from the holder 112 (i.e. extend to an upper direction in FIG. 3). Certainly, in another embodiment, the two supporting branches 114 can also form a V shape, that is to say, distances between the two supporting branches 114 become greater along a direction away from the holder 112. Of course, foil is of the Y-type flexible body 110 are not limited thereto, as long as when the Y-type gauze positioning rod 100 is located between the multi-layer structure 23 of the Y-type gauze 20, the two supporting branches 114 of the Y-type gauze positioning rod 100 are located in the two gauze branches 25 of the Y-type gauze 20.

Figure 6:
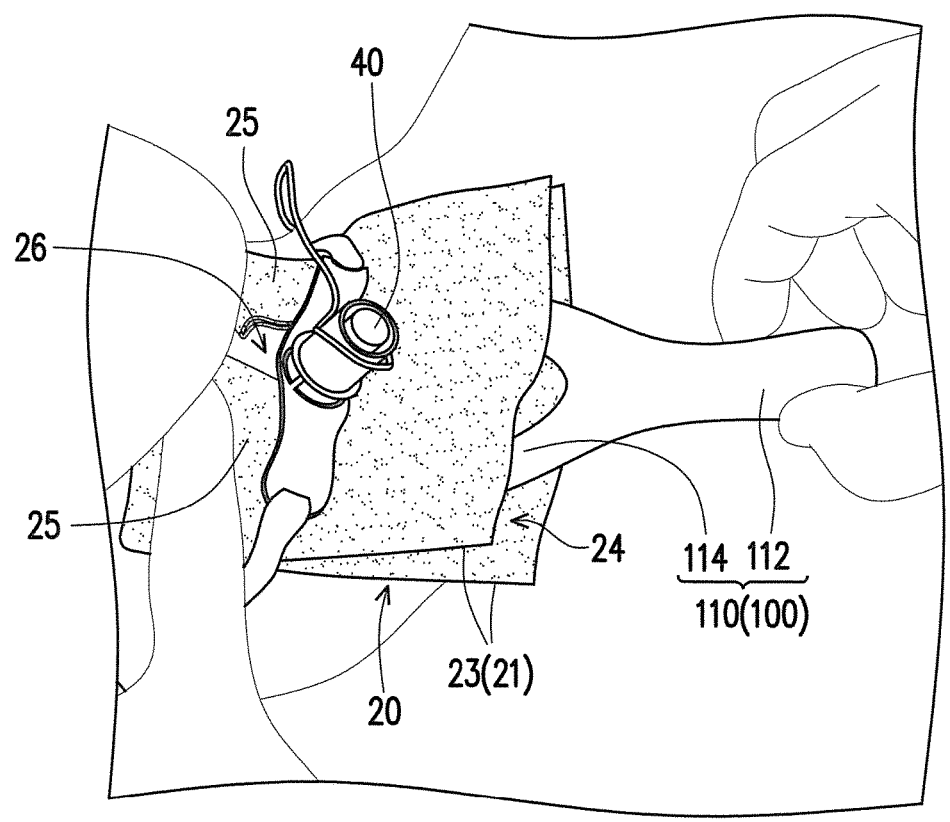
FIGS. 6 and 7 are schematic views illustrating the Y-type gauze being placed beside a tracheostomy tube by the Y-type gauze positioning rod of FIG. 1.
Figure 7:
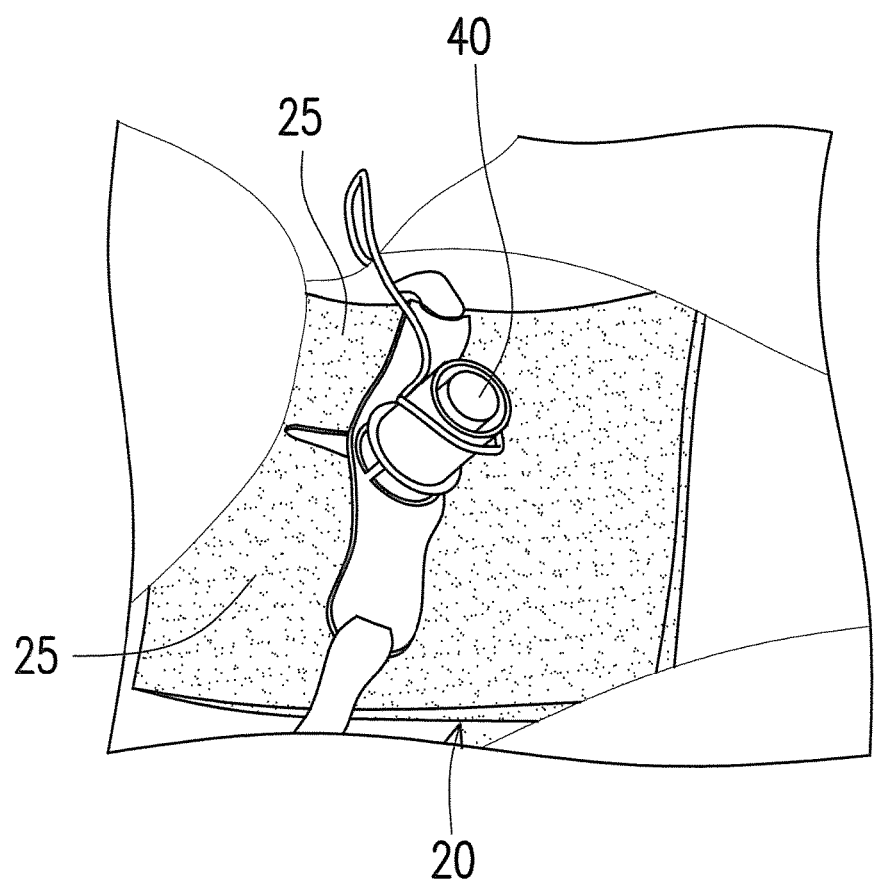

FIGS. 6 and 7 are schematic views illustrating the Y-type gauze being placed beside a tracheostomy tube by the Y-type gauze positioning rod of FIG. 1. Referring to FIGS. 6 and 7, in the embodiment, the Y-type gauze 20 includes an entrance 24 away from the cutting notch 26. After folding the gauze body 21, the entrance 24 is formed as a U shape opening, the Y-type gauze positioning rod 100 is capable of entering or exiting the Y-type gauze 20 from the entrance 24 of the Y-type gauze 20. In actual operating process, operator opens the outer packaging 30 of the Y-type gauze positioning assembly 10 shown in FIG. 1, takes out the Y-type gauze 20 and the Y-type gauze positioning rod 100, and then inserts the Y-type gauze positioning rod 100 along with the Y-type gauze 20 into a space between a tracheostomy tube 40 and the affected area. Because the Y-type gauze positioning rod 100 can be deformed slightly along the outline of the affected area, the Y-type gauze 20 and the Y-type gauze positioning rod 100 can be slid into the space between the tracheostomy tube 40 and the affected area and move to a specific position directly without moving or raising the tracheostomy tube 40.

In the embodiment, as shown in FIG. 6, because the Y-type gauze positioning rod 100 is located in the Y-type gauze 20 without fixing by adhesive, the operator only needs to press the Y-type gauze 20 gently by one hand and hold the holder 112 of the Y-type gauze positioning rod 100 by the other hand, and then pulls out the Y-type gauze positioning rod 100, and the Y-type gauze 20 can be placed to the affected area as shown in FIG. 7.

The Y-type flexible body 110 of the Y-type gauze positioning assembly 10 of the embodiment can assist the Y-type gauze 20 to be positioned quickly so as to shorten operating time and enhance working efficiency for the caregiver, lower uncomfortableness of the patient, and lower a risk of displacement or falling off of the tracheostomy tube. In the meantime, because the Y-type gauze positioning rod 100 of the Y-type gauze positioning assembly 10 can be operated easily, it is suitable for nonprofessional home caregivers. Therefore, the Y-type gauze positioning rod 100 of the Y-type gauze positioning assembly 10 can be popularized to long-term care and respiratory home care patients.

Using the conventional method which raises the tracheostomy tube by using bamboo sticks to place the Y-type gauze may cause adverse reactions (such as cough reactions) and high infection probability to patients and make patients discomfort. Comparing to the conventional method mentioned above, the Y-type gauze positioning rod 100 of the Y-type gauze positioning assembly 10 of the embodiment can prevent the issues above so as to improve patients' safety. In addition, the Y-type gauze 20 placed and positioned by the Y-type gauze positioning rod 100 of the Y-type gauze positioning assembly 10 of the embodiment can be more smooth.

It is noted that, in other embodiment, the Y-type gauze positioning rod 100 and the Y-type gauze 20 can be partially fixed by simple stitching, dispensing or other manners. In this kind of the Y-type gauze positioning assembly 10, the fixing relation of the Y-type gauze positioning rod 100 and the Y-type gauze 20 still can be released while the operator pulls out the Y-type gauze positioning rod 100 from the Y-type gauze 20. In addition, the Y-type gauze positioning rod 100 and the Y-type gauze 20 are partially fixed so as to prevent the Y-type gauze positioning rod 100 and the Y-type gauze 20 from displacing before the Y-type gauze 20 being positioned to the specific position.

Based on the above, in the Y-type gauze positioning assembly of the invention, the Y-type gauze positioning rod is disposed in the Y-type gauze as a frame. When user would like to place the Y-type gauze to the affected area, he/she only need to push the Y-type gauze positioning rod disposed in the Y-type gauze so that the Y-type gauze is moved accordingly. The Y-type flexible body of the Y-type gauze positioning rod is able to deform slightly along an outline of the affected area, therefore even a shape of the affected area is a curve, the Y-type gauze still can be moved to the affected area easily by the Y-type gauze positioning rod without raising an artificial tracheostomy tube or a blood drainage tube. In addition, the part of the holder exposed from the Y-type gauze, the user is able to pull out the Y-type gauze positioning rod directly after placing the Y-type gauze to the affected area, so that the Y-type gauze positioning rod can be removed easily. Moreover, the Y-type gauze is able to be packaged and sterilized with the Y-type gauze positioning rod so as to be combined and sold as the Y-type gauze positioning assembly.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:
1. A Y-shaped gauze positioning assembly, comprising:
a gauze; and
a Y-shaped gauze positioning rod, disposed in the gauze and comprising:
a Y-shaped flexible body having a holder and two supporting branches wherein the two supporting branches are connected to the holder and separated from each other, wherein the gauze comprises a gauze body and a cutting notch, the gauze body is folded to form a multi-layer structure having at least one crease formed on an edge of the gauze body, the cutting notch extends from the edge of the gauze body where the at least one crease exists to a center of the gauze body so as to form two gauze branches, when the Y-shaped gauze positioning rod is disposed in the multi-layer structure of the gauze, the two supporting branches of the Y-shaped gauze positioning rod are located in the two gauze branches of the gauze, and a part of the holder is exposed from the gauze.

2. The Y-shaped gauze positioning assembly as claimed in claim 1, wherein a concave is located between the two supporting branches separated with each other, a depth of the concave is greater than a length of the cutting notch of the gauze.

3. The Y-shaped gauze positioning assembly as claimed in claim 2, wherein a width of a portion of the concave corresponding to a bottom of the cutting notch ranges between 0.5 centimeter and 1 centimeter.

4. The Y-shaped gauze positioning assembly as claimed in claim 1, wherein the gauze comprises an entrance away from the cutting notch, and the two supporting branches of the Y-shaped gauze positioning rod are adapted to move into or out of the gauze from the entrance.

5. The Y-shaped gauze positioning assembly as claimed in claim 1, wherein the two supporting branches form a V shape or a U shape.

6. The Y-shaped gauze positioning assembly as claimed in claim 1, further comprising:

an outer packaging, wherein the gauze and the Y-shaped gauze positioning rod are packaged by the outer packaging and adapted to be sterilized along with the outer packaging.

* * * * *